(12) United States Patent
Lallier et al.

(10) Patent No.: US 7,507,702 B2
(45) Date of Patent: Mar. 24, 2009

(54) STABILISATION OF TRANS-1,2-DICHLOROETHYLENE

(75) Inventors: Jean-Pierre Lallier, Saint Bonnet de Mure (FR); Jessica Bains, Cholet (FR)

(73) Assignee: Arkema France, Colombes (FR)

( * ) Notice: Subject to any disclaimer, the term of this patent is extended or adjusted under 35 U.S.C. 154(b) by 118 days.

(21) Appl. No.: 10/576,702

(22) PCT Filed: Oct. 11, 2004

(86) PCT No.: PCT/FR2004/002565

§ 371 (c)(1),
(2), (4) Date: Apr. 20, 2006

(87) PCT Pub. No.: WO2005/047220

PCT Pub. Date: May 26, 2005

(65) Prior Publication Data

US 2007/0032394 A1    Feb. 8, 2007

(30) Foreign Application Priority Data

Oct. 24, 2003  (FR) .................................. 03 12434

(51) Int. Cl.
*C11D 7/50* (2006.01)
*C11D 7/40* (2006.01)

(52) U.S. Cl. .................................... 510/412; 510/408
(58) Field of Classification Search ................. 510/408, 510/412

See application file for complete search history.

(56) References Cited

U.S. PATENT DOCUMENTS

| | | | |
|---|---|---|---|
| 2,811,252 A | 10/1957 | Bachtel et al. | |
| 3,043,888 A | 7/1962 | Pray et al. | |
| 3,251,891 A | 5/1966 | Cormany et al. | |
| 4,026,956 A | 5/1977 | Manner | |
| 4,418,231 A | 11/1983 | Pamer | |
| 5,607,912 A * | 3/1997 | Samejima et al. | 510/411 |
| 6,133,221 A * | 10/2000 | Beaver et al. | 510/412 |
| 6,153,575 A | 11/2000 | Gorton | |
| 7,163,645 B2 * | 1/2007 | Hanada et al. | 252/364 |
| 7,288,511 B2 * | 10/2007 | Doyel et al. | 510/412 |

* cited by examiner

*Primary Examiner*—Gregory E Webb
(74) *Attorney, Agent, or Firm*—Steven D. Boyd

(57) ABSTRACT

The present invention relates to the stabilization of trans-1,2-dichloroethylene (TDCE) for the purpose of its use in the treatment of solid surfaces.

The stabilized solution comprises at least one acid acceptor, at least one radical scavenger, at least one Lewis base and at least one compound possessing a buffering effect.

4 Claims, No Drawings

STABILISATION OF TRANS-1,2-DICHLOROETHYLENE

FIELD OF THE INVENTION

The present invention relates to the stabilization of trans-1,2-dichloroethylene (TDCE) for the purpose of its use in the treatment of solid surfaces, more particularly for cleaning, degreasing, defluxing or drying metals.

1,2-Dichloroethylene is an industrial solvent widely used for the treatment of solid surfaces, for example for cleaning solid surfaces, degreasing metal components or defluxing printed circuits.

BACKGROUND OF THE INVENTION 1,2-Dichloroethylene exists in two isomeric forms, cis-1,2-dichloroethylene and trans-1,2-dichloroethylene. The isomers of 1,2-dichloroethylene have distinct chemical and physical properties. In particular, the trans isomer has a lower boiling point, a lower density, a lower viscosity and a lower surface tension than those of the cis isomer. This is why trans-1,2-dichloroethylene (which will be denoted by TDCE) is the preferred isomer in solvent cleaning applications. The two isomers of 1,2-dichloroethylene can be separated by fractional distillation. However, during storage, TDCE is spontaneously converted to the cis isomer, unless it is stabilized, the cis isomer being more stable thermodynamically. U.S. Pat. No. 6,153,575 discloses the use of small amounts of aliphatic aldehyde hydrazones, optionally in combination with an epoxide, for inhibiting the isomerization of TDCE to the cis isomer during storage.

The stability on storage of TDCE is its ability to withstand conversion or decomposition for a period which can range from several weeks to several months in conventional storage containers at a temperature which generally does not reach more than 50° C.

During its use as solvent for the treatment of solid surfaces, TDCE is subject to other attacks, related to the method of operation of the treatment equipment, which can result in its decomposition. The problems generated by the use of TDCE are therefore different from those encountered during storage.

The main sources of attack on TDCE during its use, for example, in a device for degreasing metal components are: air, water, metals and heat. This is because metal degreasing is generally carried out by introducing the components to be degreased into an appropriate device above the liquid level of a tank containing the TDCE maintained at reflux. The TDCE vapours condense on the metal components and the condensate is repeatedly recycled. Under these conditions, the TDCE is subjected to various reactions, such as oxidation by the air, hydrolysis by the water originating from the condensation of atmospheric water vapour, thermal decomposition or catalytic reactions on contact with the metals.

In the literature, various solutions have been provided for stabilizing some halogenated hydrocarbons confronted by the same sources of attack. The addition of various stabilizers is recommended in U.S. Pat. No. 3,043,888 for stabilizing halogenated hydrocarbons comprising from 1 to 3 carbons, more particularly trichloroethylene, during their use in metal degreasing. Some aldehyde hydrazones are particularly effective and can be used in combination with other compounds, such as aromatic compounds comprising a hydroxyl group, amines, organic epoxides, esters of monocarboxylic acids, alcohols or unsaturated compounds. Compounds which are especially effective in inhibiting the decomposition, catalysed by metals, of methylchloroform are described as being 1,3-dioxolane and its alkyl homologues or 1,4-dioxane (see U.S. Pat. Nos. 4,026,956; 3,251,891; 4,418,231 and 2,811,252).

However, the solutions provided in the literature do not include a system for stabilizing a solvent, such as a halogenated hydrocarbon, combining all the characteristics required for a stabilizer, and in particular no complete system for stabilizing with respect to air, water, metals and heat is disclosed in the prior art for TDCE.

First, the stabilizing system preferably has a two-fold action: a preventive action, more particularly in inhibiting side reactions, and a curative action, that is to say trapping in situ an undesirable effect. Subsequently, to facilitate the use of the stabilized solvent, the stabilizing system advantageously has a boiling point similar to that of the solvent, it is advantageously present in the liquid phase and in the vapour phase, it is insoluble or only slightly soluble in water and it preferably does not modify the properties of the solvent. In order not to modify the labelling of the solvent relating to the dangers of use, the stabilizing formulation is advantageously nontoxic. Finally, for economic reasons, the stabilizing formulation is preferably composed of inexpensive industrial products.

DETAILED DESCRIPTION OF THE INVENTION

It has now been found that the addition to the TDCE of several additives each having a role, such as acid acceptor, radical scavenger, Lewis base or compound possessing a buffering effect, constitutes a stabilizing system fully meeting the criteria mentioned above and makes it possible to obtain a stabilized TDCE solution which demonstrates good resistance to decomposition during its use in the treatment of metals.

During the prolonged use under hot conditions of the same TDCE feedstock, atmospheric moisture, greases, oils, dirt and fine metallic particles, in particular when the metal components are composed of aluminium or of iron, accumulate in the TDCE and are the source of various reactions which result in the decomposition of the TDCE. This is because TDCE, because of its chemical structure, can undergo mainly three types of reactivity, which are the opening of the double bond, the reactivity of the doublet of the chlorine and the production of radicals. The decomposition of TDCE generally results in the formation of hydrochloric acid or of radicals. In the presence of metals, more particularly in the presence of aluminium or of iron, hydrochloric acid can react to form aluminium chloride ($AlCl_3$) or ferric chloride ($FeCl_3$), which are in addition catalysts of the exothermic condensation reaction of TDCE. The addition of stabilizing agents, such as acid acceptors, radical scavengers, Lewis bases or buffering agents, makes it possible to have a preventive and/or curative action with regard to these various reactions.

A subject-matter of the invention is thus a stabilized solution of trans-1,2-dichloroethylene (TDCE) comprising, as additives, at least one acid acceptor, at least one radical scavenger, at least one Lewis base and at least one compound possessing a buffering effect.

Mention may more particularly be made, among the acid acceptors which can be used in the stabilized solution according to the invention, of organic epoxides. Mention may be made, as nonlimiting examples, of ethylene oxide, propylene oxide, butylene oxide, butadiene monoxide, butadiene dioxide, epichlorohydrin, glycidol, isobutylene oxide or isopropyl glycidyl ether. Use will preferably be made of propylene oxide, butylene oxide or isopropyl glycidyl ether.

In the context of the present invention, use may be made, as radical scavengers, of various organic compounds, such as alkenes, heterocycles or phenol derivatives. Mention may be made, as nonlimiting examples of alkenes, of diisobutylene, amylene, isoprene or α-methylstyrene. Mention may be made, as nonlimiting examples of heterocycles, of pyrroles, more particularly N-methylpyrrole, 1,4-dioxane or furans, more particularly tetrahydrofuran. Mention may be made, as nonlimiting examples of phenol derivatives, of phenol, thymol or ionol.

It would not be departing from the scope of the present invention to use a first radical scavenger for the vapour phase and a second radical scavenger for the liquid phase. For example, isoprene can be used as radical scavenger for the vapour phase and diisobutylene as radical scavenger for the liquid phase. This combination of two scavengers has the advantage of being simultaneously effective with regard to the liquid TDCE and with regard to the vapour TDCE, which is necessary for the application envisaged.

The Lewis bases, compounds which donate electron pairs, make it possible to saturate the Lewis acid sites of the metals and thus to inhibit the reaction for the formation of $AlCl_3$ or $FeCl_3$. The Lewis bases which can be used in the stabilized solution according to the invention are highly varied in nature. Mention may be made of acetals, ketones, nitro compounds, esters of carboxylic acids or ethers. Methylal will be preferred as acetals. Mention may be made, as nonlimiting examples of ketones, of acetone and methyl ethyl ketone. Mention may be made, as nonlimiting examples of nitro compounds, of nitromethane or nitroethane. Mention may be made, as nonlimiting examples of esters of carboxylic acids, of methyl formate, methyl acetate or isopropyl acetate. tert-Butyl methyl ether will be preferred as ether.

Amines are more particularly suitable among the compounds possessing a buffering effect which can be used in the present invention. Amines make it possible to obtain a pH which is sufficiently basic to limit the kinetics of decomposition of the solvent and to maintain a relatively constant pH. Any amine may be used and use will preferably be made of triethylamine, N-methylmorpholine, diethylamine or N,N-diisopropylamine.

It would not be departing from the scope of the invention to use, in addition to the compounds mentioned above, an alcohol to block $AlCl_3$ or $FeCl_3$ after their possible formation. The alcohols which may be suitable are, for example, methanol, ethanol, n-butanol or tert-butanol.

Generally, the additives present in a stabilizing system have a boiling point in the vicinity of that of TDCE. However, compounds which are slightly less volatile than TDCE can be chosen which make it possible to specifically stabilize the liquid phase of TDCE or, conversely, more volatile compounds can be chosen in order to effectively stabilize the vapour phase of TDCE.

The amount of each of the additives present in a stabilized solution of TDCE can vary greatly but the content of each additive in the stabilized solution will preferably be between 10 and 10 000 ppm, preferably between 10 and 1 000 ppm. The total amount of additives should be sufficient to inhibit the decomposition of TDCE under the usual conditions of use for the treatment of metals, without detrimentally affecting the properties of the solvent. It is considered that an overall content of additives of less than 50 000 ppm and preferably of less than 5 000 ppm makes it possible to obtain a stable TDCE solution which is simultaneously effective in the treatment of metals and the most economic possible.

More particularly, a stabilized solution comprises from 200 ppm to 800 ppm of an acid acceptor, from 100 to 700 ppm of a radical scavenger or of a mixture of radical scavengers, from 10 to 100 ppm of a Lewis base and from 10 to 50 ppm of a compound possessing a buffering effect.

A stabilized solution of TDCE according to the invention comprises butylene oxide, diisobutylene, isoprene, acetone and diethylamine. More particularly, the stabilized solution comprises from 200 ppm to 800 ppm, preferably 530 ppm, of butylene oxide, from 50 to 500 ppm, preferably 200 ppm, of diisobutylene, from 50 to 200 ppm, preferably 100 ppm, of isoprene, from 10 to 100 ppm, preferably 50 ppm, of acetone and from 10 to 50 ppm, preferably 10 ppm, of diethylamine.

Experimental Part

Various tests, the principles of which are set out below, are used to evaluate the effectiveness of the stabilization of TDCE:

Hydrolysis test: The test consists in monitoring the change in the pH of the stabilized solution to be tested, to which 1% of water is added, during heating at reflux for 100 hours. For this, use is made of a 500 ml three-necked flask surmounted by a thermometer and a Liebig condenser. The third opening is equipped with a septum through which samples can be withdrawn using a syringe. 247.5 ml of solution to be tested are introduced into the round-bottomed flask with 2.5 ml of water. The solution is heated at reflux for 100 hours. Samples of approximately 5 to 10 ml are withdrawn every 2-3 hours and the pH of the withdrawn solution is measured after addition of an equivalent amount of water at pH 7. The hydrolysis test is negative if the variation in the pH over time is not significant.

Scratch test: It is based on Standard ASTM D 2943-96.2000. It consists in evaluating the stability of a chlorinated solvent in the presence of a prescratched aluminium sheet. The scratch test is negative if no corrosive reaction occurs.

BAM (Bundesanstalt für Materialprüfung—Berlin) Test

The stabilization of a formulation with regard to aluminium is tested by virtue of the BAM test, which is divided into several experiments.

A 500 ml three-necked flask surmounted by a Liebig condenser is used. The temperature of the sample is measured using a probe.

100 ml of solution to be tested are introduced into the three-necked flask with 100 ml of toluene, 18 g of aluminium powder and 0.7 g of anhydrous $AlCl_3$. The mixture, known as BAM 1, is heated at reflux for 2 times 9 hours. It is observed whether a change in coloration or an exothermic reaction occurs.

A second experiment is carried out under the same experimental conditions as above after having added 1 g of zinc stearate to the BAM 1 mixture. This is the BAM 2 reaction medium.

A third experiment is carried out with a mixture prepared from the BAM 1 mixture to which 10 ml of oleic acid are this time added. The reaction mixture is known as BAM 3.

If, during the tests carried out on the 3 mixtures BAM 1, BAM 2 and BAM 3, no change in coloration is observed or if no exothermic reaction occurred, an experiment referred to as BAM 4 is carried out. It consists in separating the solution to be tested into three fractions of the same size by distillation. 100 ml of toluene, 18 g of aluminium powder and 0.7 g of anhydrous $AlCl_3$ are added to 100 ml of each fraction and then the fractions are heated at reflux for 2 times 9 hours. The test is negative if no reaction occurs during the heating and if no change in coloration appears.

The following examples illustrate the invention without limiting it.

EXAMPLE 1 (COMPARATIVE)

The hydrolysis test is carried out on a TDCE solution from PPG Industries which comprises 30 ppm of butylene oxide. A change in the pH, which changes from an initial value of 7.17 to a value of 7.97 after a period of 100 hours, is observed. This solution cannot therefore be regarded as stable.

EXAMPLE 2

TDCE from PPG Industries is used to prepare a stabilized TDCE solution which comprises 530 ppm of butylene oxide, 300 ppm of diisobutylene, 50 ppm of acetone and 10 ppm of N-methylmorpholine.

The hydrolysis test shows that the pH undergoes only a slight variation, between 7.8 and 7.94, over a period of 100 hours.

During the scratch test, no reaction is observed; the aluminium is not attacked by the solution under the conditions of the test.

Under the conditions of the BAM test, the solution does not react in any of the reaction media BAM 1, BAM 2 and BAM 3, since no exothermic reaction is observed. Only a slight translucent yellow coloration in the BAM 1 medium and a greenish coloration in the BAM 2 medium are observed. According to the BAM 4 test, 3 fractions of approximately equal amount were collected, corresponding respectively to the 3 temperature ranges 39-41° C., 41-41.3° C. and 41.3-44° C. None of the 3 fractions reacts in the reaction medium. An exothermic reaction is not observed but only a slight greenish coloration for the first fraction.

EXAMPLE 3

TDCE from PPG Industries is used to prepare a stabilized TDCE solution which comprises 530 ppm of butylene oxide, 200 ppm of diisobutylene, 100 ppm of isoprene, 50 ppm of acetone and 10 ppm of diethylamine.

The pH during the hydrolysis test carried out on this solution remains constant: the initial pH is 8.75. After 100 hours, it is equal to 8.79. This solution is more basic than the solution of Example 2. During the scratch test, no reaction is observed; the aluminium is not attacked by the solution under the conditions of the test.

Under the conditions of the BAM test, the solution does not react in any of the reaction media BAM 1, BAM 2 and BAM 3 since no exothermic reaction is observed. Only a slight translucent yellow coloration in the BAM 1 medium and the BAM 2 medium is observed. According to the BAM 4 test, 3 fractions of approximately equal amount were collected, corresponding respectively to the 3 temperature ranges 36.5-37.8° C., 37.8-38° C. and 38-38.2° C. An exothermic reaction or a change in coloration is not observed for any of the fractions.

The invention claimed is:

1. Stabilized solution of trans-1,2-dichloroethylene comprising, trans-1,2-dichloroethylene and as additives, butylene oxide, diisobutylene, isoprene, acetone and diethylamine.

2. Solution according to claim 1, characterized in that the content of each additive in the stabilized solution is between 10 and 10 000 ppm.

3. Solution according to claim 1, characterized in that the overall content of additives is less than 50 000 ppm.

4. Solution according to claim 1, characterized in that said additives comprise: from 200 to 800 ppm of butylene oxide, from 100 to 500 ppm of diisobutylene, from 50 to 200 ppm of isoprene, from 10 to 100 ppm of acetone and from 10 to 50 ppm of diethylamine.

* * * * *